United States Patent

Okumura et al.

[11] 4,022,620
[45] May 10, 1977

[54] METHOD OF FORMING COLOR PHOTOGRAPHIC IMAGES

[75] Inventors: Akio Okumura; Atsushi Sugizaki; Seiji Ichijima; Keisuke Shiba; Kiyoshi Nakazyo, all of Minami-ashigara, Japan

[73] Assignee: Fuji Photo Film Co., Ltd., Minami-ashigara, Japan

[22] Filed: Apr. 3, 1975

[21] Appl. No.: 564,977

[30] Foreign Application Priority Data

Apr. 3, 1974 Japan .............................. 49-37651

[52] U.S. Cl. .................... 96/56.2; 96/56.5; 96/100; 260/309.5
[51] Int. Cl.² ...................... G03C 7/00; G03C 1/40
[58] Field of Search ................. 96/100, 56.2, 56.5, 96/100 N

[56] References Cited

UNITED STATES PATENTS 3,730,722  5/1973  Inoue et al. ..................... 96/56.3

FOREIGN PATENTS OR APPLICATIONS 2,213,461  11/1972  Germany ........................... 96/100

*Primary Examiner*—J. Travis Brown
*Attorney, Agent, or Firm*—Sughrue, Rothwell, Mion, Zinn & Macpeak

[57] ABSTRACT

A method of forming color photographic images which comprises developing image-exposed photographic silver halide emulsion layer with a primary aromatic amino color developing agent in the presence of a yellow color forming coupler represented by the following general formula (I)

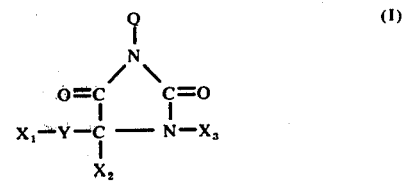

wherein $X_1$ represents a hydrogen atom, an alkyl group, an aryl group, a heterocyclic group or an acyl group; $X_2$ represents a hydrogen atom, an alkyl group or an aryl group; $X_3$ represents a hydrogen atom, an alkyl group, an aryl group or an acyl group; Y represents an oxygen atom or a sulfur atom; and Q represents a residue of a yellow color forming coupler, e.g., a yellow coupler in which one hydrogen atom attached to the active methylene group of the coupler is eliminated. These yellow color forming couplers provide yellow color images having superior properties.

35 Claims, No Drawings

METHOD OF FORMING COLOR PHOTOGRAPHIC IMAGES

BACKGROUND OF THE INVENTION

1. Field of the Invention

The present invention relates to a method of forming color photographic images, and more particularly to a method of forming color photographic images using a novel yellow color forming coupler.

2. Description of the Prior Art

It is well known that color forming couplers couple with oxidation products of primary aromatic amino developing agents to form color photographic images. Most conventional yellow color forming couplers are four-equivalent couplers and these couplers require four moles of exposed silver halide as an oxidizing agent to form one mole of azomethine dye. An introduction of a large amount of silver halide into light-sensitive layers leads to some disadvantages such as an increase in light scattering in the emulsion layers and consequently, a decrease in sharpness of the images formed, and in addition, an increase in the processing time for the light-sensitive materials due to an increase in the thickness of the emulsion layers. Furthermore, the formation of dyes with these couplers is not completed during color development and thus it is necessary to use strong oxidizing agents in subsequent processing steps to complete the dye formation.

In order to improve these defects, two-equivalent yellow color forming couplers have been employed, which require only two moles of exposed silver halide to form one mole of azomethine dye.

The two-equivalent yellow color forming couplers, in general, have chemical structures in which one of the hydrogen atoms of the active methylene group is substituted with a releasable atom or group. Examples of such releasable atoms or groups are a fluorine atom as described in U.S. Pat. No. 3,277,155, a phenoxy group as described in U.S. Pat. No. 3,408,194, an acyloxy group as described in U.S. Pat. No. 3,447,928, a sulfoxy group as described in U.S. Pat. No. 3,415,652, and a group having a saccharin structure as described in U.S. Pat. No. 3,730,722.

However, these couplers are not sufficient for use in color photography because they are accompanied by disadvantages in that the coupling reactivity is insufficient, in that a marked color fog is produced, in that the couplers per se are unstable and their coupling activities decrease or color stain occurs in the light-sensitive materials during storage, in that the yellow color images formed are unstable or in that the preparation of the couplers is quite difficult.

As couplers which improve these defects, there are the yellow color forming couplers having a releasable group derived from imide compounds described, for example, in Japanese Patent Application OPI Nos. 26,133/1972, 29,432/1973 and 73,147/1973.

However, use of these couplers is still accompanied by either of the following undesirable properties. That is, developed silver which is formed during the color development step of color processing is not removed completely in subsequent processing steps using a bleaching bath and a fixing bath or in a subsequent processing step using a blixing bath containing a silver complex forming agent and an oxidizing agent and remains in the final photographs to adversely affect the color reproduction. The coupler does not provide a sufficiently high color density without using a color developer solution containing benzyl alcohol which tends to increase the biological oxygen demand (BOD) and it is undesirable to use benzyl alcohol in view of environmental pollution, particularly, water pollution. The sufficient color density which is required for providing good color reproduction can not be obtained where a relatively small amount of a high boiling solvent for the coupler, which is used to dissolve the coupler and is incorporated into a photographic material together with the coupler, is employed. The photographic properties of a color image obtained are markedly influenced by variations in the pH of the color developer solution used.

SUMMARY OF THE INVENTION

An object of the present invention is to provide novel yellow color forming couplers which are suitable for use in the color photographic process based on the subtractive process for color reproduction.

Another object of the present invention is to provide a method of forming dye images by developing a silver halide emulsion in the presence of a novel yellow color forming coupler.

Another object of the present invention is to provide a color photographic light-sensitive material which has a silver halide emulsion layer containing a novel yellow color forming coupler.

Another object of the present invention is to provide a color developer solution containing a novel yellow color forming coupler.

Still another object of the present invention is to provide a means for reducing the amount of silver halide contained in a photographic emulsion and improving the sharpness of the images formed by the use of a novel yellow color forming coupler.

Still another object of the present invention is to provide a means for improving the color reproduction and the transparency of the images obtained by the use of a novel yellow color forming coupler which does not adversely affect easy and rapid removal of developed silver, which is formed during a color development step, in a bleaching step and a fixing step or in a blixing step, in which both bleaching and fixing steps are carried out in a single bath.

Still another object of the present invention is to provide a color photographic light-sensitive material which is well suited for use in a rapid color processing using a blixing bath containing both a weak oxidizing agent and a silver complex forming agent.

A further object of the present invention is to provide a stable color photographic light-sensitive material which is less sensitive to variation in pH and the amount of benzyl alcohol in a color developer solution and can be subjected to a wide range of color processings, by the use of a novel yellow color forming coupler.

A still further object of the present invention is to provide yellow color images which have spectral absorption characteristics suitable for the subtractive process for color reproduction and excellent stability.

These and other objects of the present invention will become apparent from the following detailed description as set forth below.

It has now been found that the above-described objects have been achieved by developing an image-exposed photographic silver halide emulsion layer with a primary aromatic amino color developing agent to form a dye image, in the presence of a yellow color forming coupler represented by the following general formual (I)

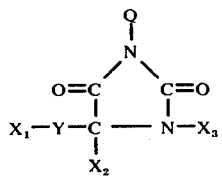

wherein $X_1$ represents a hydrogen atom, an alkyl group, an aryl group, a heterocyclic group or an acyl group; $X_2$ represents a hydrogen atom, an alkyl group or an aryl group; $X_3$ represents a hydrogen atom, an alkyl group, an aryl group or an acyl group; Y represents an oxygen atom or a sulfur atom, and Q represents a residue of a yellow color forming coupler in which one hydrogen atom attached to the active methylene group of the yellow forming coupler has been eliminated.

DETAILED DESCRIPTION OF THE INVENTION

In the general formula (I), the alkyl group represented by $X_1$, $X_2$, or $X_3$ can be a straight-chain or branched-chain or in the form of ring and an unsubstituted or substituted alkyl group having up to about 35 carbon atoms including the carbon atoms in the substituents is suitable. Examples of suitable alkyl group substituents are an alkenyl group, an aryl group (for example, phenyl, methylphenyl, etc.), an alkoxy group (for example, methoxy, ethoxy, dodecyloxy, etc.), an aryloxy group (for example, phenoxy, methylphenoxy, etc.), an alkoxycarbonyl group (for example, methoxycarbonyl, hexadecyloxycarbonyl, etc.), an acylamino group (for example, acetamido, α-(3-pentadecylphenoxy)butyramido, etc.), a carboxy group, a hydroxy group, an amino group (for example, amino, N-ethylamino, N,N-dimethylamino, N-butyl-N-octylamino, anilino, etc.), a carbamoyl group (for example, methylcarbamoyl, dodecylcarbamoyl, etc.), a sulfamoyl group (for example, methylsulfamoyl, diethylsulfamoyl, N-γ-(2,4 -di-tert-amylphenoxy)propylsulfamoyl, etc.), a cyano group, a halogen atom (for example, fluorine, chlorine, bromine, etc.) and the like.

Specific examples of suitable alkyl groups for $X_1$, $X_2$ and $X_3$ include methyl, ethyl, propyl, isopropyl, amyl, isoamyl, hexyl, 1-methylpentyl, 2-methylpentyl, heptyl, 1-methylhexyl, 2-methylhexyl, 3-methylhexyl, 5-methylhexyl, octyl, 2-ethylhexyl, nonyl, isononyl, decyl, undecyl, dodecyl, tetradecyl, hexadecyl, octadecyl, cyclohexyl, benzyl, phenethyl, allyl, oleyl, 2-methoxyethyl, 2-hydroxyethyl, carboxymethyl, 2-carboxyethyl, 3-phenoxypropyl, 2-(4-tert-butylphenoxy)isopropyl, cinnamyl, and the like.

Further, $X_2$ and $X_3$ can combine with each other to form a 5-membered or a 6-membered ring. Examples of suitable rings formed by $X_2$ and $X_3$ include a pyrrolidine ring, a piperidine ring, and the like.

Suitable aryl groups represented by $X_1$, $X_2$ or $X_3$ include a phenyl group, a naphthyl group and the like, and these aryl groups can also be substituted. Examples of aryl group substituents are an alkyl group, an aryl group, an alkoxy group, an aryloxy group, an alkoxycarbonyl group, an acylamino group, a carboxy group, a hydroxy group, an amino group, a carbamoyl group, a sulfamoyl group, a cyano group, a nitro group, a halogen atom, and the like.

The heterocyclic group represented by $X_1$ is bonded to the oxygen atom or the sulfur atom represented by Y through one carbon atom forming the heterocyclic ring. Examples of such heterocyclic rings include a 2-tetrahydropyranyl group, a 2-pyridyl group, a 4-pyridyl group, and the like.

Suitable acyl groups represented by $X_1$ or $X_3$ are acyl groups having up to 35 carbon atoms. Examples of such acyl groups include acetyl, propionyl, octanoyl, tetradecanoyl, stearoyl, benzoyl, α-(2,4-di-tert-amylphenoxy)butyryl, and the like.

Suitable yellow color forming coupler residues represented by Q include a residue of an open-chain ketomethylene type compound in which one of the hydrogen atoms on the carbon atom of the coupling position, i.e., the carbon atom of the active methylene group directly connected to two carbonyl groups is eliminated, and includes an α-acylacetamide coupler.

Of the yellow color forming couplers which can be used in the present invention, those yellow color forming couplers represented by the following general formula (II) are suitable:

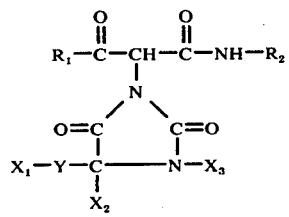

wherein $R_1$ represents an aliphatic group, an aromatic group or a heterocyclic group, $R_2$ represents an aromatic group or a heterocyclic group; and $X_1$, $X_2$, $X_3$ and Y each has the same meaning as defined in the general formula (I).

In the general formula (II), suitable aliphatic groups represented by $R_1$ include an aliphatic group having up to about 25 carbon atoms such as an unsubstituted or substituted alkyl group which can be a straight-chain or a branched-chain or in the form of a ring.

Suitable substituents for the alkyl group for $R_1$ are an alkenyl group, an aryl group, an alkoxy group, an aryloxy group, an acyl group, an amino group, a carboxy group, an acylamino group, a carbamoyl group, an imido group, an alkoxycarbonyl group, an acyloxy group, a sulfo group, a sulfonyl group, a sulfonamido group, a sulfamoyl group, and the like, and which in turn can be further substituted.

Suitable specific examples of aliphatic groups for $R_1$ are as follows: methyl, ethyl, propyl, isopropyl, butyl, isobutyl, tert-butyl, amyl, isoamyl, tert-amyl, hexyl, 1-methylpentyl, 2-methylpentyl, neopentyl, 1,1-dimethylbutyl, heptyl, 1-methylhexyl, 2-methylhexyl, 3-methylhexyl, 5-methylhexyl, 1,1-dimethylhexyl, octyl, 2-ethylhexyl, 1,1-diethylhexyl, nonyl, isononyl, decyl, undecyl, dodecyl, tetradecyl, hexadecyl, octadecyl, 1,1-dimethylnonyldecyl, 1,1-diamylhexyl, 1-methyl-1-nonyldecyl, cyclopropyl, cyclobutyl, cyclopentyl, cyclohexyl, benzyl, phenethyl, allyl, oleyl, 7,7-dimethylnorbornyl, 1-methylcyclohexyl, 2-methoxyisopropyl, 2-benzylisopropyl, 2-phenoxyisopropyl, 2-p-tert-butylphenoxyisopropyl, 2-naphthoxyisopropyl, cinnamyl, α-aminoisopropyl, α-(N,N-diethylamino)-isopropyl, α-(succinimido)isopropyl, α-(phthalimido)isopropyb, α-(benzenesulfonamido)isopropyl, and the like.

Examples of aromatic groups represented by $R_1$ and $R_2$ include an unsubstituted or substituted phenyl group. Suitable substituents include monovalent substituents such as a halogen atom, a nitro group, a cyano group, a thiocyano group, a hydroxy group, an alkoxy group, an aryloxy group, an acyloxy group, an alkyl group, an alkenyl group, an aryl group, an amino group, a carboxy group, an acyl group, an alkoxycarbonyl group, an aryloxycarbonyl group, a carbamoyl group, an acylamino group, an imido group, a sulfo group, an alkxylsulfonyl group, an arylsulfonyl group, an alkoxy sulfonyl group, an aryloxysulfonyl group, a sulfamoyl group, a sulfonamido group, a ureido group, a thioureido group, and the like, and also divalent substituents which can form a condensed ring together with the phenyl group. Examples of condensed rings formed by phenyl groups having such a divalent substituent are a naphthyl group, a quinolyl group, an isoquinolyl group, a chromanyl group, a coumaranyl group, a tetrahydronaphthyl group, etc. These monovalent and divalent substituents can, in turn, have additional substituents.

The heterocyclic groups represented by $R_1$ and $R_2$ are bonded through one carbon atom forming the heterocyclic ring to the carbon atom of the carbonyl group of the acyl group and the nitrogen atom of the amido group in the α-acylacetamide represented by the general formula (II), respectively. Such heterocyclic groups include a thiophene group (for example, 2-thienyl, 3-thienyl, 2-benzothienyl, 3-benzothienyl, 2-naphthothienyl, 3-naphthothienyl, etc.), a furan group (for example, 2-furyl, 3-furyl, 2-benzofuranyl, 3-benzofuranyl, 1-isobenzofuranyl, 3-isobenzofuranyl, etc.), a pyran group (for example, 3-pyranyl, 4-pyranyl, 5-pyranyl, 6-pyranyl, etc.), a chromene group (for example, 3-chromenyl, 4-chromenyl, etc.), a pyrrole group, a pyrazole group, a pyridine group (for example, 2-pyridyl, 3-pyridyl, 4-pyridyl, etc.), a quinoline group (for example, 2-quinolyl, 3-quinolyl, 4-quinolyl, 1-isoquinolyl, 3-isoquinolyl, 4-isoquinolyl, etc.), the pyrazine group (for example, 2-pyrazinyl, 2-quinoxalinyl, etc.), a pyrimidine group (for example, 2-pyrimidinyl, 4-pyrimidinyl, 5-pyrimidinyl, 2-quinazolinyl, 4-quinazolinyl, etc.), a pyridazine group (for example, 3-pyridazinyl, 4-pyridazinyl, 3-cinnolinyl, 4-cinnolinyl, etc.), an indolizine group (for example, 1-indolizinyl, 2-indolizinyl, 3-indolizinyl, 5-indolizinyl, 6-indolizinyl, 7-indolizinyl, etc.), a perimidine group (for example, 2-perimidinyl, etc.), a thiazole group (for example, 2-thiazolyl, 2-benzothiazolyl, 3-isothiazolyl, 4-isothiazolyl, 5-isothiazolyl, etc.), an imidazole group (for example, 2-benzoimidazolyl, etc.), an oxazole group (for example, 2-oxazoly, 4-oxazolyl, etc.), a 1,3,5-triazine group (for example, 1,3,5-triazinyl, etc.), an oxazine group, and the like. These heterocyclic groups can be unsubstituted or substituted with a halogen atom, a nitro group, a cyano group, a thiocyano group, a hydroxy group, an alkoxy group, an aryloxy group, an acyloxy group, an alkyl group, an alkenyl group, an aryl group, an amino group, a carboxy group, an acyl group, an alkoxycarbonyl group, an aryloxycarbonyl group, a carbamoyl group, an acylamino group, an imido group, a sulfo group, an alkylsulfonyl group, an arylsulfonyl group, an alkoxysulfonyl group, an aryloxysulfonyl group, a sulfamoyl group, a sulfonamido group, a ureido group, a thioureido group, and the like.

It should be understood that the yellow color forming couplers represented by the general formula (II) which can be used in the present invention also include compounds in which two coupler residues are bonded to each other through $R_1'$ or $R_2'$, i.e., a divalent group of the monovalent groups previously described for $R_1$ or $R_2$ in the general formula (II). In such case, the yellow color forming couplers can have the following general formulas (IIa) or (IIb):

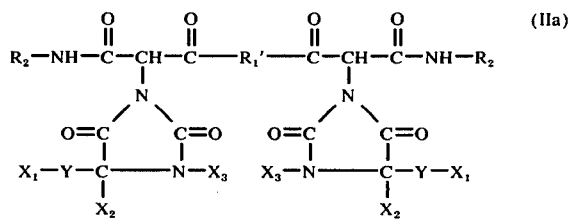

(IIa)

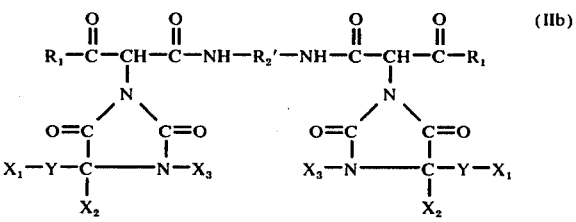

(IIb)

in which $R_1$, $R_2$, $X_1$, $X_2$, $X_3$ and Y each has the same meaning as defined in the general formula (II); and $R_1'$ ad $R_2'$ each represents a divalent group corresponding to $R_1$ and $R_2$, respectively, in the general formula (II).

Yellow color forming couplers in which $R_1$ in the above-described general formula (II) is an alkyl group in which a tertiary carbon atom is bonded to the carboxyl group, particularly, a tert-butyl group, are preferred. Also, yellow color forming couplers in which $R_1$ is a phenyl group or a phenyl group substituted with an electron-donating group such as an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an amino group (for example, amino, N,N-dimethylamino, N-butyl-N-octylamino, etc.) are preferred.

Yellow color forming couplers in which $R_2$ in the above-described general formula (II) is a phenyl group in which one of the ortho positions is substituted with a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino, etc.), are preferred.

Of the yellow color forming couplers which can be used in the present invention, the compounds represented by the following general formulas (III) and (IV) are particularly preferred.

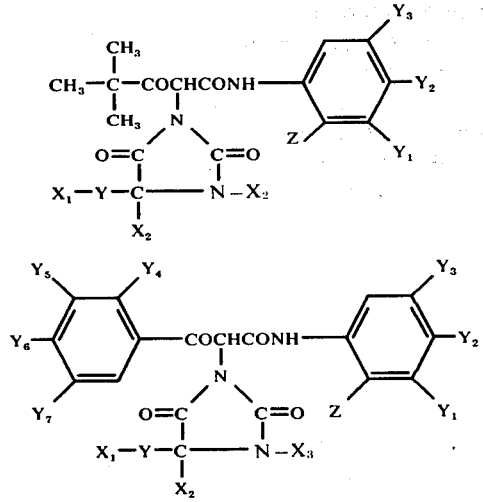

(III)

(IV)

in which $X_1$, $X_2$, $X_3$ and Y each has the same meaning as defined in the general formula (I), and Z represents a halogen atom (for example, fluorine, chlorine, bormine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino, etc.), $Y_1$, $Y_2$ and $Y_3$, which may be the same or different, each represents a hydrogen atom, a halogen atom (for example, fluorine, chlorine, bromine, etc.), an alkyl group (for example, methyl, ethyl, octadecyl, etc.), an alkenyl group (for example, allyl, etc.), an alkoxy group (for example, methoxy, ethoxy, dodecyloxy, etc.), an aryl group (for example, phenyl, methylphenyl, etc.), an arylamino group (for example, anilino, etc.), an acylamino group (for example, acetamido, α-3-pentadecylphenoxy)-butyramido, etc.), a sulfonamido group (for example, methylsulfonamido, α-3-pentadecylphenoxy)propylsulfonamido, etc.), a carbamoyl group (for example, carbamoyl, N-methylcarbamoyl, N-γ-(2,4-di-tert-amylphenoxy)propylcarbamoyl, N,N-diethylcarbamoyl, N-ω-(2,4-di-tert-amylphenoxy)butylcarbamoyl, etc.), a sulfamoyl group (for example, sulfamoyl, N-methylsulfamoyl, N-γ-(2,4-di-tert-amylphenoxy)propylsulfamoyl, N,N-diethylsulfamoyl, N-ω-(2,4-di-tert-amylphenoxy)butylsulfamoyl, etc.), an alkoxycarbonyl group (for example, ethoxycarbonyl, dodecyloxycarbonyl, hexadecyloxycarbonyl, etc.), a carboxy group, a sulfo group, a cayano group or a hydroxy group, $Y_4$, $Y_5$, $Y_6$ and $Y_7$, which may be the same or different, each represents a hydrogen atom, an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), an amino group (for example, amino, N,N-dimethylamino, N-butyl-N-octylamino, etc.), or an acylamino group (for example, acetamido, α-(2,4-di-tert-amylphenoxy)butyramido, etc.).

Representative examples of yellow color forming couplers which can be used in the present invention are illustrated below.

1. α-Pivaloyl-α-(5-methoxyl-1-phenyl-3-hydantoinyl)-2-methoxy-5-[N-γ-(2,4-di-tert-amylphenoxy)propylsulfamoyl]acetanilide
2. α-Pivaloyl-α-(1-benzyl-5-methoxy-3-hydantoinyl)-2-chloro-5-[γ-(2,4-di-tert-amylphenoxy)-butyramido]acetanilide
3. α-Benzoyl-α-(5-methoxy-3-hydantoinyl)-2-methoxyacetanilide
4. α-[2-Methyl-2-(4-methylphenoxy)propionyl]-α-(5-ethoxy-5-phenyl-3-hydantoinyl)-2-chloro-5-[α-(3-pentadecylphenoxy)-butyramido]acetanilide
5. α-(4-Methoxybenzoyl)-α-(1-benzyl-5-methoxy-3-hydantoinyl)-2-chloro-5-[γ-(2,4-di-tert-amylphenoxy)butyramido]acetanilide
6. α-(4-Methoxybenzoyl)-α-(5-methoxy-1-methyl-3-hydantoinyl)-2-chloro-5-[α-(2,4-di-tert-amylphenoxy)butyramido]acetanilide
7. α-(2-Methylbenzoyl)-α-(1-benzyl-5-methoxy-3-hydantoinyl)-2-chloro-5-dodecyloxycarbonylacetanilide
8. α-Pivaloyl-α-(1-methyl-5-methoxy-3-hydantoinyl)-2-chloroacetanilide
9. α-(4-Methoxybenzoyl)-α-(1-benzyl-5-methoxy-3-hydantoinyl)-2-chloro-5-[α-(2,4-di-tert-amylphenoxy)butyramido]acetanilide
10. α-{3-[α-(2,4-Di-tert-amylphenoxy)butyramido]-4-methoxybenzoyl}-α-(5-phenoxy-3-hydantoinyl)-2-methoxy-5-N,N-diethylsulfamoylacetanilide
11. α-Pivaloyl-α-(5-methoxy-5-phenyl-3-hydantoinyl)-2-chloro-5-[γ-(2,4-di-tert-amylphenoxy)-butyramido]acetanilide
12. α-(2-Ethylmercapto-2-methylpropionyl)-α-(1-benzyl-5-methoxy-3-hydantoinyl)-2-methoxy-5-[N-γ-(2,4-di-tert-amylphenoxy)propylsulfamoyl]acetanilide
13. α-Pivaloyl-α-[1-propyl-5-(2-pyridyloxy)-3-hydantoinyl]-2-methoxy-5-hexadecyloxycarbonylacetanilide
14. α-(4-Stearoylaminobenzoyl)-α-(5-methoxy-5-methyl-3-hydantoinyl)-3,5-dicarboxyacetanilide
15. α-Benzoyl-α-{5-[2-(2-methoxyethoxy)ethoxy]-3-hydantoinyl}-2-chloro-5-dodecyloxycarbonylacetanilide
16. α-(4-Methoxybenzoyl)-α-(5-ethoxy-5-methyl-3-hydantoinyl)-2-chloro-5-[α-(2,4-di-tert-amylphenoxy)butyramido]-acetanilide
17. α-Pivaloyl-α-(1-acetyl-5-methoxy-3-hydantoinyl)-2-chloro-5-[α-(2,4-di-tert-amylphenoxy)-butyramido]acetanilide
18. α-Pivaloyl-α-(5-benzyloxy-1-methyl-3-hydantoinyl)-2-chloro-5-[γ-(2,4-di-tert-amylphenoxy)-butyramido]acetanilide
19. α-(2-Furoyl)-α-(5-methoxy-1-methyl-3-hydantoinyl)-2-chloro-5-[α-(2,4-di-tert-amylphenoxy)-butyramido]acetanilide
20. α-Pivaloyl-α-[5-(4-carboxyphenoxy)-1-methyl-3-hydantoinyl]-2-chloro-5-[γ-(2,4-di-tert-amylphenoxy)butyramido]-acetanilide
21. α-(4-Methoxybenzoyl)-α-[5-(4-chlorophenylthio)-1-propyl-3-hydantoinyl]-2-chloro-5-[α-(2,4-di-tert-amylphenoxy)-butyramido]acetanilide
22. α-Pivaloyl-α-(5-ethylthio-1-methyl-3-hydantoinyl)-2-chloro-4-[N-ω-(2,4-di-tert-amylphenoxy)butylsulfamoyl]acetanilide
23. α-(4-Methoxybenzoyl)-α-(5-hydroxy-5-methyl-3-hydantoinyl)-2-chloro-5-[α-(2,4-di-tert-amylphenoxy)butyramido]-acetanilide
24. α-Pivaloyl-α-(5-hydroxy-5-methyl-3-hydantoinyl)-2-chloro-5-[α-(2,4-di-tert-amylphenoxy)-butyramido]acetanilide 25. α-Pivaloyl-α-(5-hydroxy-5-methyl-3-hydantoinyl)-2-chloro-5-[γ-(2,4-di-tert-amylphenoxy)-butyramido]acetanilide
26. α-(4-Methoxybenzoyl)-α-(5-dodecyloxy-1-methyl-3-hydantoinyl)-3,5-dicarboxyacetanilide
27. α-(4-Methoxybenzoyl)-α-(5-methoxy-5-phenyl-3-hydantoinyl-2-chloro-5-[γ-(2,4-di-tert-amylphenoxy)butyramido]-acetanilide The yellow color forming couplers of the present invention, in general, can be prepared by reacting a halogenated compound in which one of the hydrogen atoms attached to the active methylene group of a corresponding four-equivalent coupler is substituted with a halogen atom, preferably a chlorine atom or a bromine atom, with a hydantoin derivative in the presence of a base, for example, an inorganic base such as potassium hydroxide, sodium hydroxide, etc., or an organic base such as triethylamine, diazobicyclooctane, etc. The reaction can be carried out in an appropriate organic solvent at a temperature of about 10° to 70° C. The reaction time is not critical. Examples of organic solvents which can be used in this invention are alcohols such as methanol, ethanol, isopropanol, etc., halogenated hydrocarbons such as chloroform, methylchloroform, etc., hydrocarbons such as ligroin, hexane, etc., aromatic hydrocarbons such as benzene, toluene, xylene, etc., amides such as dimethylformamide, diethylacetamide, hexamethylphosphoramide, N-methyl-2-pyrrolidone, tetramethylurea, etc., sulfoxides such as dimethylsulfoxide, etc., acetonitrile, or the like, preferably dimethylformamide, dimethylsulfoxide. Specific examples of 4-equivalent yellow color forming couplers are described in, for example, U.S. Pat. Nos. 2,875,057, 3,265,506, 3,277,155, 3,408,194, 3,409,439, 3,415,652, 3,447,928, 3,551,155, 3,551,156, 3,582,322, 3,685,995, etc. The halogenated compound which can be used in the preparation of the yellow color forming couplers of the present invention can be prepared by the method as described in U.S. Pat. Nos. 2,728,658 and 3,447,928. More specifically, the methods which are described in Japanese Patent Application (OPI) Nos. 94,661/1974 and 102,663/1974 can be employed. The hydantoin derivative can be prepared according to the methods described in *Bulletin of the Chemical Society of Japan*, Vol. 39, page 1562 (1966) and *Journal of Heterocyclic Chemistry*, Vol. 7, page 1289 (1970).

The preparation of the representative examples of yellow color forming couplers of this invention is hereinafter illustrated in greater detail. Unless otherwise indicated herein, all parts, percents, ratios and the like are by weight.

SYNTHESIS EXAMPLE 1

Preparation of α-Pivaloyl-α-(1-benzyl-5-methoxy-3-hydantoinyl)-2-chloro-5-[γ-(2,4-di-tert-amylphenoxy)butyramido]-acetanilide [Coupler (2)]

To a solution containing 4.6 g of potassium hydroxide dissolved in 20 ml of methanol, was added a solution containing 18.2 g of 1-benzyl-5-methoxyhydantoin dissolved in 100 ml of dimethylformamide, and further a solution containing 25 g of α-pivaloyl-α-chloro-2-chloro-5-[γ-(2,4-di-tert-amylphenoxy)-butyramido]acetanilide dissolved in 100 ml of dimethylformamide was added dropwise thereto. After being stirred for 2 hours at 25° C, the reaction mixture was poured into 2 l of water, and extracted with 1 l of ethyl acetate. The ethyl acetate layer was separated, washed with a dilute hydrochloric acid solution, washed with water and dried over anhydrous sodium sulfate. The ethyl acetate was distilled off under reduced pressure, and the residue was recrystallized from a solvent mixture of hexane and ethyl acetate, yielding 18 g of Coupler (2). The melting point was 106° ∼ 108° C.

SYNTHESIS EXAMPLE 2

Preparation of α-(4-Methoxybenzoyl)-α-(1-benzyl-5-methoxy-3-hydantoinyl)-2-chloro-5-[γ-(2,4-di-tert-amylphenoxy)-butyramido]acetanilide [Coupler (5)]

The same procedures as described in Synthesis Example 1 were carried out except for the use of 20 g of α-(4-methoxybenzoyl)-α-bromo-2-chloro-5-[γ-(2,4-di-tert-amylphenoxy)-butyramido]acetanilide in place of the α-pivaloyl-α-chloro-2-chloro-5-[γ-(2,4-di-tert-amylphenoxy)butyramido]acetanilide. The product was recrystallized from methanol to obtain 19 g of Coupler (5). The melting point was 135° ∼ 137° C.

SYNTHESIS EXAMPLE 3

Preparation of α-(4-Methoxybenzoyl)-α-(1-benzyl-5-methoxy-3-hydantoinyl)-2-chloro-5-[α-(2,4-di-tert-amylphenoxy)-butyramido]acetanilide [Coupler (9)]

The same procedures as described in Synthesis Example 1 were carried out except for the use of 20 g of α-(4-methoxybenzoyl)-α-bromo-2-chloro-5-[α-(2,4-di-tert-amylphenoxy)-butyramido]acetanilide in place of the α-pivaloyl-α-chloro-2-chloro-5-[γ-(2,4-di-tert-amylphenoxy)butyramido]acetanilide. The product was recrystallized from a solvent mixture of ethyl acetate and hexane to obtain 18 g of Coupler (9). The melting point was 158° ∼ 160° C.

SYNTHESIS EXAMPLE 4

Preparation of α-(4-methoxybenzoyl)-α-(5-methoxy-5-phenyl-3-hydantoinyl)-2-chloro-5-[γ-(2,4-di-tert-amylphenoxy)-butyramido]acetanilide [Coupler (27)]

The same procedures as described in Synthesis Example 2 were carried out except for the use of 17 g of 5-methoxy-5-phenylhydantoin in place of 1-benzyl-5-methoxyhydantoin. The product was recrystallized from a solvent mixture of ethyl acetate and hexane to obtain 19.5 g of Coupler (27). The melting point was 189° ∼ 191° C.

The yellow color forming couplers according to the present invention can be employed in photographic light-sensitive materials or color developer solutions. Diffusible couplers, such as Coupler (3), are suitably added to color developer solutions used to color develop the light-sensitive materials used for color photography to form yellow color images.

Non-diffusible couplers, such as Coupler (1) which contains a ballasting group in the molecule, are suitable for use by incorporation into photographic light-sensitive materials. Such couplers can be incorporated into photographic emulsions according to the methods using a high boiling and/or a low boiling organic solvent as described in U.S. Pat. Nos. 2,304,939, 2,322,027, 2,801,170, 2,801,171, 2,949,360, 3,253,921 and 3,574,627. Non-diffusible couplers, such as Coupler (14) which has a ballasting group as well as a water solubilizing group such as a carboxy group or a sulfo group, are suitable for use by incorporating into photographic light-sensitive materials. Such couplers can be incorporated into a photographic emulsion in the form of an alkaline aqueous solution thereof.

The terms "diffusible", "non-diffusible" and "ballasting group" as used herein are employed as they are conventionally used in the art with respect to color forming couplers and are well understood by one of ordinary skill in the art.

Using the yellow color forming couplers according to the present invention in light-sensitive materials, if the amount incorporated is very small, a large amount of silver halide is required to produce the desired color density, and thus the thickness of the emulsion layer tends to be high, which results in not only increasing the time required for processing but in addition in increasing the light scattering in the silver halide emulsion layer reducing the sharpness of the images produced. On the other hand, if the amount of the coupler incorporated is very large, the couplers which are not converted into the dyes at color development remain in the emulsion layer and reduce the efficiency of coupler utilization. This is disadvantageous from an economical standpoint and results in an increase in the thickness of the emulsion layer accompanied by the above-described disadvantages. Accordingly, the coupler of this invention is preferably employed in a range of from about 0.02 to about 1.0 mole per mole of silver halide in the emulsion layer.

The yellow color forming couplers according to the present invention can be used individually or as a mixture of two or more. Furthermore, they can be employed together with other color forming couplers out of the scope of the present invention.

The photographic light-sensitive materials which provide yellow color images using the yellow color forming coupler according to the present invention can include other two-equivalent or four-equivalent couplers.

Preferred examples of such couplers are those having a ballasting group as described in U.S. Pat. Nos. 2,920,961, 2,875,057, 3,418,129, 3,658,544, 3,681,076, 3,062,653 and 2,474,293; British Pat. No. 1,201,943; German Patent Application OLS No. 2,216,578; and Japanese Pat. Application Nos. 35,379/1973 and 69,383/1973, and the like.

Suitable yellow couplers are those couplers described in U.S. Pat. Nos. 3,265,506, 2,728,658, 3,369,895, 3,582,322, 3,408,194, 3,415,652, 3,253,924 and 3,510,306; British Pat. Nos. 1,286,411, 1,040,710, 1,302,398 and 1,204,680; German Patent Application OLS Nos. 1,956,281, 2,162,899, 2,213,461, and 2,263,875, and the like.

Suitable magenta couplers are those couplers described in U.S. Pat. Nos. 2,600,788, 3,558,319, 3,468,666, 3,419,391, 3,311,476, 3,253,924, and 3,311,476; British Pat. Nos. 1,293,640; Japanese Patent Publication No. 13,111/1969; Japanese Patent Application Nos. 114,445/1972, 114,446/1972, 21,454/1973 and 45,971/1973, and the like.

Suitable cyan couplers are those couplers described in U.S. Pat. Nos. 2,369,929, 2,474,293, 3,591,383, 2,895,826, 3,458,315, 3,311,476, 3,419,390, 3,476,563, 3,253,924, 3,002,836, and 3,542,552; British Pat. No. 1,201,110 and the like.

Also, colored couplers such as those described in U.S. Pat. Nos. 2,434,272, 3,476,564 and 3,476,560; Japanese Patent Application No. 45971/1973; U.S. Pat. Nos. 3,034,892, 3,386,301 and 2,434,272, and the like can be employed.

In the present invention, various kinds of DIR compounds can be used. For example, illustrative DIR couplers are those DIR couplers described in U.S. Pat. Nos. 3,148,062, 3,227,554, 3,701,783, 3,617,291 and the like.

Examples of DIR magenta couplers are those couplers described in U.S. Pat. Nos. 3,148,062, 3,227,554, 3,701,783 and 3,617,291; Japanese Patent Application No. 33,238/73, and the like.

Illustrative DIR cyan couplers are those couplers described in U.S. Pat. Nos. 3,418,062, 3,227,554, 3,701,783, 3,617,291 and 3,622,328; Japanese Patent Publication No. 28,836/1970; German Patent Application OLS No. 2,163,811; Japanese Patent Application No. 33,238/1973 and the like, DIR hydroquinones such as those described in U.S. Pat. Nos. 3,379,529, 3,639,417 and 3,297,445; Japanese Patent Application No. 87,723/1973, and the like and non-color forming DIR compounds such as those described in U.S. Pat. Nos. 3,632,345 and 3,227,554, and the like are illustrated.

Also, non-color forming couplers such as those described in British Pat. Nos. 861,138, 914,145 and 1,109,963; Japanese Patent Publication No. 14,033/1970; U.S. Pat. No. 3,580,722; *Mitteilungen aus den Forschungslaboratorien der Agfa, Leverkusen*, Vol. 4, pages 352 ~ 367 (1964), and the like, can be used.

Furthermore, according to the present invention, competing couplers such as those described in British Pat. Nos. 861,138, 1,204,964 and 904,365; U.S. Pat. Nos. 3,174,862, 3,520,690, 2,742,832, 3,560,212, 3,645,737 and 2,689,793; Japanese Patent Publication Nos. 9,505/1969, 9,506/1969 and 9,507/1969, and the like, can be included in an emulsion layer or in a developer.

According to the present invention, yellow color images can be formed during color development in the presence of the yellow color forming coupler of the present invention, used either in a light-sensitive material and/or in a color developer solution. The coupler of this invention can be used in an amount of from about 0.5 to about 10 g, preferably 1 to 5 g, per liter of the color developer solution. The photographic light-sensitive materials containing the yellow color forming coupler of the present invention are subjected to an image exposure and then developed with a color developer solution containing a primary aromatic amino developing agent. Alternatively, photographic light-sensitive materials are subjected to image exposure and then developed with a color developer solution containing the yellow color forming coupler according to the present invention together with a primary aromatic amino developing agent.

The photographic light-sensitive materials which are used in the present invention can be conventional photographic light-sensitive materials containing silver halide as a light-sensitive substance.

The silver halide photographic emulsion which can be used in the present invention comprises a light-sensitive silver halide such as silver chloride, silver bromide, silver chlorobromide, silver iodobromide, silver chloroiodide, silver chloroiodobromide, and the like, dispersed in a hydrophilic polymer, and can be prepared by various known methods. For example, a single jet method, a double jet method, a controlled double jet method, and the like, can be employed. A mixture of two or more silver halide emulsions which are prepared separately can also be used. The silver halide grains can have a homogeneous crystal structure, a layered structure in which the interior differs from the outer layer of the grain, or the so-called conversion-type silver halide grains as described in British Pat. No. 635,841 and U.S. Pat. Nos. 2,592,250 and 3,622,318. Silver halide grains which form latent image predominantly on the surface of the grains or predominantly in the interior of the grains can also be used. These photographic emulsions are described, for example, in C. E. K. Mees & T. H. James, *The Theory of the Photographic Process*, 3rd Ed. MacMillan, New York (1966); and P. Grafikides, *Chimie Photographique*, Paul Montel, Paris, (1957), and can be prepared by known methods such as an ammonia method, a neutral method and an acid method.

After the formation of the silver halide grains, the emulsion can be washed with water in order to remove the by-produced water-soluble salts (for example, potassium nitrate where silver bromide is formed from silver nitrate and potassium bromide), and then ripened by heating in the presence of a chemical sensitizer such as sodium thiosulfate, N,N,N'-trimethylthiourea, a thiocyanate complex of monovalent gold, a thiosulfate complex of monovalent gold, stannous chloride, hexamethylenetetramine, and the like, to increase the sensitivity without coarsening the grains. General methods for these chemical sensitization techniques are described in the above-mentioned references.

Specific examples of suitable chemical sensitizers include, for example, gold compounds such as chloroaurates and gold trichloride as described in U.S. Pat. Nos. 2,399,083, 2,540,085, 2,597,856 and 2,597,915; salts of a noble metal, such as platinum, palladium, iridium, rhodium and ruthenium, as described in U.S. Pat. Nos. 2,448,060, 2,540,086, 2,566,245, 2,566,263 and 2,598,079; sulfur compounds capable of forming silver sulfide by reacting with a silver salt, such as those described in U.S. Pat. Nos. 1,574,944, 2,410,689, 3,189,458 and 3,501,313; stannous salts, amines, and other reducing compounds such as those described in U.S. Pat. Nos. 2,487,850, 2,518,698, 2,521,925, 2,521,926, 2,694,637, 2,983,610 and 3,201,254, and the like.

Various kinds of conventional stabilizers or anit-fogging agents can be added to the photographic emulsions used in the present invention in order to prevent a reduction in the sensitivity or a formation of fog. A wide variety of such compounds are known such as heterocyclic compounds, mercury-containing compounds, mercapto compounds or metal salts, including 4-hydroxy-6-methyl-1,3,3a,7-tetraazaindene, 3-methylbenzothiazole and 1-phenyl-5-mercaptotetrazole. Examples of these compounds which can be used are described, for example, in U.S. Pat. Nos. 1,758,576, 2,110,178, 2,131,038, 2,173,628, 2,697,040, 2,304,962, 2,324,123, 2,394,198, 2,444,605~8, 2,566,245, 2,694,716, 2,697,099, 2,708,162, 2,728,663~5, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668 and 3,622,339; and British Pat. Nos. 893,428, 403,789, 1,173,609 and 1,200,188.

The photographic emulsions can be spectrally sensitized or supersensitized using a cyanine dye such as cyanine, merocyanine, carbocyanine or styryl dyes, either individually or in combination. Spectral sensitization techniques are well known, and are described, for example, in U.S. Pat. Nos. 2,493,748, 2,519,001, 2,977,229, 3,480,434, 3,672,897, 3,703,377, 2,688,545, 2,912,329, 3,397,060, 3,615,635 and 3,628,964; British Pat. Nos. 1,195,302, 1,242,588 and 1,293,862; German Patent Application OLS Nos. 2,030,326 and 2,121,780; Japanese Patent Publication Nos. 4,936/1968, 14,030/1969 and 10,773/1968; U.S. Pat. Nos. 3,511,664, 3,522,052, 3,527,641, 3,615,613, 3,615,632, 3,617,295, 3,635,271 and 3,694,217; and British Pat. Nos. 1,137,580 and 1,216,203, and the like. The spectral sensitizers can be chosen as desired depending on the spectral range, sensitivity, and the like depending on the purpose and uses of the photographic materials to be sensitized.

Examples of hydrophilic colloids which can be used as a binder for the silver halide grains include, for example, gelatin, colloidal albumin, casein, a cellulose derivative such as carboxymethylcellulose and hydroxyethylcellulose, a polysaccharide derivative such as agar-agar, sodium alginate and a starch derivative, a synthetic hydrophilic colloid such as polyvinyl alcohol, poly-N-vinyl pyrrolidone, polyacrylic acid copolymers and polyacrylamide, or the derivatives or partially hydrolyzed products thereof. If desired, compatible mixtures of these colloids can also be employed. Of these colloids, gelatin is most commonly used. It can be replaced partially or completely by a synthetic polymer, by a so-called gelatin derivative such as those prepared by reacting or modifying the amino, imino, hydroxy or carboxy groups contained, as functional groups, in the gelatin molecule with a compound containing a group capable of reacting with the above-described groups, or a graft gelatin such as those prepared by grafting another polymer chain on the gelatin molecule.

Examples of suitable compounds which can be used for the preparation of the above-described gelatin derivatives include isocyanates, acid chlorides and acid anhydrides such as those described in U.S. Pat. No. 2,614,928; acid anhydrides such as those described in U.S. Pat. No. 3,118,766; bromoacetic acids such as those described in Japanese Patent Publication No. 5,514/1964; phenyl glycidyl ethers such as those described in Japanese Patent Publication No. 26,845/1967; vinylsulfones such as those described in U.S. Pat. No. 3,132,945; N-allylvinylsulfonamides such as those described in British Pat. No. 861,414; maleinimides such as those described in U.S. Pat. No. 3,186,846; acrylonitriles such as those described in U.S. Pat. No. 2,594,293; polyalkylene oxides such as those described in U.S. Pat. No. 3,312,553; epoxy compounds such as those described in Japanese Patent Publication No. 26,845/1967; esters such as those described in U.S. Pat. No. 2,763,639; and alkane sultones such as those described in British Pat. No. 1,033,189.

A wide variety of polymers or copolymers can be employed as polymers to be grafted to gelatin including those obtained from the so-called vinyl monomers such as acrylic acid, methacrylic acid or derivatives thereof, e.g., the esters, amides and nitriles thereof; or styrene. Other examples of suitable polymers are described in U.S. Pat. Nos. 2,763,625, 2,831,767 and 2,956,884; *Polymer Letters*, Vol. 5, page 595 (1967); *Phot. Sci. Eng.*, Vol. 9, page 148 (1965); and *J. Polymer Sci.*, Part A-1, Vol. 9, page 3,199 (1971). Hydrophilic polymers or copolymers having a certain degree of compatibility with gelatin such as those prepared from acrylic acid, methacrylic acid, acrylamide, methacrylamide, hydroxyalkylacrylates, hydroxyalkylmethacrylates, and the like are particularly desirable.

The hydrophilic layers which constitute the photographic light-sensitive materials of the present invention can be hardened using conventional methods. Examples of suitable hardeners include, for example, an aldehyde type compound such as formaldehyde and glutaraldehyde; a ketone compound such as diacetyl and cyclopentadione; a reactive halogen-containing compound such as bis(2-chloroethylurea), 2-hydroxy-4,6-dichloro-1,3,5-triazine and those described in U.S. Pat. Nos. 3,288,775 and 2,732,303; and British Pat. Nos. 974,723 and 1,167,207; a reactive olefin containing compound such as divinyl sulfone, 5-acetyl-1,3-diacryloylhexahydro-1,3,5-triazine and those described in U.S. Pat. Nos. 3,635,718 and 3,232,763; and British Pat. No. 994,869; and N-methylol compound such as N-hydroxymethylphthalimide and those described in U.S. Pat. Nos. 2,732,316 and 2,586,168; an isocyanate compound such as those described in U.S. Pat. No. 3,103,473; an aziridine compound such as those described in U.S. Pat. Nos. 3,017,280 and 2,983,611; an acid derivative such as those described in U.S. Pat. Nos. 2,725,294 and 2,725,295; a carbodiimide compound such as those described in U.S. Pat. No. 3,100,704; an epoxy compound such as those described in U.S. Pat. No. 3,091,537; an isooxazole compound such as those described in U.S. Pat. Nos. 3,321,313 and 3,543,292; a halocarboxyaldehyde such as mucochloric acid; a dioxane derivative such as dihydroxydioxane and dichlorodioxane; and an inorganic hardener such as chrome alum and zirconium sulfate. Instead of the above compounds, precursors of hardeners such as the alkali metal bisulfite-aldehyde adducts, methylol derivatives of hydantoin, primary fatty nitroalcohols and the like can also be used.

The photographic layers which constitute the photographic light-sensitive materials of the present invention can be applied to a substantially planar material which does not undergo any severe dimensional change during processing, for example, a rigid support such as glass, metal or ceramics, or a flexible support as desired. Representative flexible supports include those generally employed for photographic materials, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, a thin glass film and paper. A baryta coated paper, a paper which is coated or laminated with an α-olefin polymer, particularly those obtained from a monomer having from 2 to 10 carbon atoms, such as polyethylene, polypropylene and ethylene-butene copolymers, and a synthetic resin film in which the adhesiveness to other polymers and the printing properties are improved by roughening the surfaces thereof, such as is described in Japanese Patent Publication No. 19,068/1972 can also be used to advantage as a support.

These supports can be transparent or opaque, depending on the purposes of the photographic materials. Colored transparent supports which contain a dye or pigment can also be used. Such colored supports have been utilized in X-ray films, and are described in *J. SMPTE*, Vol. 67, page 296 (1958).

Examples of opaque supports include opaque films produced by incorporating into a transparent film a dye or a pigment such as titanium oxide and zinc oxide, or surface-treated plastic films such as those described in Japanese Patent Publication No. 19,068/1972, as well as intrinsically opaque materials such as paper. Highly light-shielding papers and synthetic resin films containing, for example, carbon black or dyes can also be used. When the adhesion between a support and a photographic layer is unsatisfactory, a subbing layer adhesive to both the support and the photographic layer can be provided on the support. The surfaces of the support can also be pre-treated by a corona discharge, a UV radiation treatment, a flame treatment and the like in order to further improve the adhesion.

The photographic layers can be applied to a support using various conventional coating methods, including, for example, a dip coating method, an air-knife coating method, a curtain coating method and an extrusion coating method using the hopper described in U.S. Pat. No. 2,681,294. If desired, two or more layers can be coated simultaneously using the methods as described in U.S. Pat. Nos. 2,761,791, 3,508,947, 2,941,898 and 3,526,528. A suitable coating amount of the silver halide can range from about $4 \times 10^{-4}$ to about $4 \times 10^{-2}$ mole/m$^2$, preferably $2 \times 10^{-3}$ to $2 \times 10^{-2}$ mole/m$^2$.

The photographic light-sensitive materials which can be used in the present invention comprise one or more silver halide emulsion layers on a support. Color photographic light-sensitive materials conventionally have a blue-sensitive silver halide emulsion layer, a green-sensitive silver halide emulsion layer, and a red-sensitive silver halide emulsion layer. The silver halide emulsion layer can be divided into two or more layers which are sensitive to substantially the same spectral region. The photographic light-sensitive materials of the present invention can include in addition to the silver halide emulsion layers, substantially light-insensitive layers including conventional layers such as a surface protective layer, a filter layer, an intermediate layer, an antihalation layer, a barrier layer, an anti-curling layer, a backing layer, and the like.

The yellow color forming couplers according to the present invention can be used by incorporating the couplers into various photographic light-sensitive materials. For example, these couplers can be used in multilayer color photographic light-sensitive materials such as those described in U.S. Pat. Nos. 3,582,322, 3,622,318, 3,547,640, 3,672,898, 3,516,831, 3,705,799~803, 3,715,208, 3,737,312, 3,703,375, 3,379,529, 3,402,046, 3,620,747 and 3,450,536; British Pat. No. 923,045; Japanese Patent Application Nos. 108,438/1970 and 29,835/1969. These couplers can also be employed in photographic light-sensitive materials suitable for use in a color diffusion transfer process as described in British Pat. Nos. 840,731 and 904,364; and U.S. Pat. No. 3,227,551.

Any light sources can be employed for exposing the photographic light-sensitive materials.

The aromatic primary amino developing agents which can be used in the method of forming photographic images of the present invention include those which have a primary amino group on the aromatic ring and which develop exposed silver halide, and precursors of these compounds.

Suitable color developing agents include o-aminophenols, p-aminophenols, N,N-disubstituted-o-phenylenediamines, and in particular, N,N-disubstituted-p-phenylenediamines. Specific examples of these color developing agents are 4-amino-3-dimethylamino-N,N-diethylaniline, 4-amino-3-ethoxy-N,N-diethylaniline, 4-amino-3,5-dimethyl-N,N-diethylaniline, 4-amino-3-methyl-N,ethyl-N-(β-hydroxyethyl)aniline, 4-amino-3-methyl-N,N-diethylaniline, 4-amino-3-methyl-N-ethyl-N-(β-methanesulfonamidoethyl)-aniline, 4-amino-3-(β-methanesulfonamidoethyl)-N,N-diethylaniline, 4-amino-N-ethyl-N-(β-hydroxyethyl)aniline, 4-amino-N,N-diethyl aniline, 4-amino-N-ethyl-N-ω-sulfobutylaniline, 4-amino-3-methyl-N-ethyl-N-(β-methoxyethyl)aniline, 4-amino-3-methyl-N-ethyl-N-(β-ethoxyethyl)aniline, and the like.

These aromatic primary amino developing agents are described, for example, in U.S. Pat. Nos. 2,193,015 and 2,592,364; Japanese Patent Application OPI No. 64,933/1973; and L. F. A. Mason, *Photographic Processing Chemistry*, pages 226 ~ 229, Focal Press, London (1966). They can be used, if desired, together with 3-pyrazolidones.

The color developer solution can contain various additives, if desired. Typical examples of these additives include alkali agents (for example, alkali metal or ammonium hydroxides, carbonates or phosphates and the like; pH-adjusting agents or buffers (for example, weak acids such as acetic acid and boric acid; weak bases; salts thereof; and the like)); developing accelerators (for example, various pyridinium compounds or cationic compounds such as those described in U.S. Pat. Nos. 2,648,604 and 3,671,247; potassium nitrate; sodium nitrate; condensation products of polyethylene glycol and their derivatives, such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides; alkali metal iodides; nitrobenzimidazoles such as those described in U.S. Pat. Nos. 2,496,940 and 2,656,271; mercaptobenzimidazole; 5-methylbenzotriazole; 1-phenyl-5-mercaptotetrazole; compounds for use in rapid processing solution such as those described in U.S. Pat. Nos. 3,113,864, 3,342,596, 3,295,976, 3,615,522 and 3,597,199; thiosulfonyl compounds such as those described in British Pat. No. 972,211; phenazine-N-oxides such as those described in Japanese Patent Publication No. 41,675/1971; those described in *Kagaku Shashin Binran* (*Manual of Scientific Photography*), Vol. II, pages 29 ~ 47 and the like); stain or sludge preventing agents such as those described in U.S. Pat. Nos. 3,161,513 and 3,161,514; and British Pat. Nos. 1,030,442, 1,144,481 and 1,251,558; interlayer-effect accelerators as disclosed in U.S. Pat. No. 3,536,487; preservatives (for example), sulfites, bisulfites hydroxyamine hydrochloride, formsulfite, alkanolamine-sulfite adducts, etc.) and the like.

After color development, the color photographic materials are subjected to a bleaching. The bleaching can be simultaneously carried out together with the fixing. A bleaching bath can be converted to a blixing bath by adding a fixing agent, if desired. Many compounds can be used as a bleaching agent. Of these bleaching agents, ferricyanides; bichromates; water-soluble cobalt (III) salts, water-soluble copper (II) salts; water-soluble quinones; nitrosophenol; compounds of a polyvalent metal such as iron (III); cobalt (III); copper (II), etc., especially, complex salts of such a polyvalent cation, and an organic acid, for example, an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and 2,6-dipicolinic acid; peracids such as alkylperacids, persulfaes, permanganates and peroxides; hypochlorites; chlorine; bromine; and the like can be suitably used, individually or in combination. To the bleaching solution, bleaching accelerators such as those described in U.S. Pat. Nos. 3,042,520 and 3,241,966; and Japanese Patent Publication Nos. 8,506/1970 and 8,836/1970 and various other additives can be employed.

Using the yellow color forming couplers according to the present invention, the amount of silver halide added to a photographic medium can be reduced resulting in an improvement in the image sharpness. Also, according to the present invention, silver images which are formed during color development are easily and rapidly removed in a bleaching step and a fixing step or in a blixing step in which both bleaching and fixing steps are carried out in a single bath, and thus photographic images of superior color reproduction and clearness are obtained. Further using the yellow color forming couplers of the present invention, color photographic light-sensitive materials can be obtained which are suitable for rapid color processing using a blixing bath containing both a weak oxidizing agent and a silver complex forming agent. Furthermore, using the yellow color forming couplers of the present invention, stable color photographic light-sensitive materials which are less sensitive to variation in pH and the amount of benzyl alcohol in a color developer solution can be obtained and can be subjected to a wide range of color processings.

The yellow color forming couplers of the present invention can be used in conventional silver halide color photographic light-sensitive materials (for example, color negative films, color positive films, color printing papers, color reversal films, color direct positive films, and the like) and in photographic light-sensitive materials for the color diffusion transfer process.

The present invention will now be illustrated in greater detail by reference to the following examples, but the present invention is not intended to be interpreted as being limited to these examples.

EXAMPLE 1

A solution prepared by heating at 40° C a mixture of 63.0 g of the above-described Coupler (5), α-(4-methoxybenzoyl)-α-(1-benzyl-5-methoxy-3hydantoinyl)-2-chloro-5-[γ-(2,4-di-tert-amylphenoxy)-butyramido]acetanilide, 60 ml of di-n-butyl phthalate and 120 ml of ethyl acetate was added to 600 ml of an aqueous solution containing 60 g of gelatin and 3.0 g of sodium p-dodecyl-benzene sulfonate and the mixture was stirred, then, passed five times through a preheated colloid mill.

All of the coupler dispersion thus-prepared was added to 1 kg of a photographic emulsion containing 70 g of gelatin and 57.1 g of silver iodobromide (iodide content: 5.0 mole%), and then 13 ml of a 4% aqueous solution of the sodium salt of 2-hydroxy-4,6-dichloro-s-triazine, as a hardener, was added. After adjusting the pH to 6.5, the mixture was coated on a cellulose triacetate film in a dry thickness of 6.0 microns to prepare a photographic light-sensitive material. This material was designated Sample A. In Sample A, the coupler content coated was $20.0 \times 10^{-4}$ mol/m$^2$ and the coating amount of silver was $87.0 \times 10^{-2}$ g/m$^2$.

For comparison, a photographic light-sensitive material was prepared by carrying out the same procedure as described for Sample A except for preparing a coupler dispersion using 46.5 g of Coupler (a), α-(4-methoxybenzoyl)-2-chloro-5-[γ-(2,4-di-tert-amyl-phenoxy)acetanilide in place of Coupler (5), 45 ml of di-n-butyl phthalate and 90 ml of ethyl acetate, mixing the coupler dispersion with 2 kg of the same photographic emulsion and adding 20.5 ml of the same aqueous solution of the hardener. This material was designated Sample B. The coating amount of silver was $187.0 \times 10^{-2}$ g/m$^2$.

For further comparison, a photographic light-sensitive material was prepared by carrying out the same procedure as described for Sample A except that 60.5 g of Coupler (b), α-(4-methoxybenzoyl)-α-(1-benzyl-3-hydantoinyl)-2-chloro-5-[γ-(2,4-di-tert-amylphenoxy)butyramido]acetanilide, which is a coupler of the type described in Japanese Patent Application OPI No. 29,432/1973 was used in place of Coupler (5). This material was designated Sample C. In Sample C the coupler content coated was $20.4 \times 10^{-4}$ mol/m$^2$ and the coating amount of silver was $88.2 \times 10^{-2}$ g/m$^2$.

These photographic light-sensitive materials were subjected to stepwise exposure and processed in the following manner.

| Processing Step | Temperature (° C) | Time (min) |
| --- | --- | --- |
| 1. Color Development | 20 | 15 |
| 2. Wash | 18 | 1 |
| 3. First Fixing | 20 | 4 |
| 4. Wash | 18 | 3 |
| 5. Bleaching | 20 | 5 |
| 6. Wash | 18 | 3 |
| 7. Second Fixing | 20 | 3 |
| 8. Wash | 18 | 15 |

The composition of the color developer solution used was as follows:

| Color Developer Solution A | |
| --- | --- |
| Sodium Sulfite (anhydrous) | 3.0 g |
| 4-Amino-3-methyl-N,N-diethylaniline Hydrochloride | 2.5 g |
| Sodium Carbonate (monohydrate) | 47.0 g |
| Potassium Bromide | 2.0 g |
| Water to make | 1,000 ml |

The fixing solution used was an acidic aqueous solution containing sodium thiosulfate and sodium sulfite, and the bleaching solution used was a neutral aqueous solution containing potassium ferricyanide and potassium bromide.

After processing Samples A, B and C, the transmission optical density to blue light was measured and the photographic properties obtained are shown in Table 1.

TABLE 1

| Sample | Coupler | Coating Amount of Coupler (mol/m$^2$) | Fog | Sensi-*tivity | Gamma | Maximum Density |
| --- | --- | --- | --- | --- | --- | --- |
| A | (5) | $20.2 \times 10^{-4}$ | 0.20 | 100 | 2.86 | 3.46 |
| B | Comparison Coupler (a) | $21.8 \times 10^{-4}$ | 0.13 | 96 | 1.89 | 2.81 |
| C | Comparison Coupler (b) | $20.4 \times 10^{-4}$ | 0.23 | 100 | 2.77 | 3.40 |

*Relative value of exposure amount required to produce a density of fog + 0.10

Referring to Samples A, B and C, the maximum densities to blue light were measured which were obtained upon treatment for different periods of color development processing time. The results shown in Table 2 were obtained.

TABLE 2

| Sample | Coupler | AgX/Coupler (mole ratio) | Developing Time (min) | | | |
| --- | --- | --- | --- | --- | --- | --- |
| | | | 5 | 10 | 15 | 20 |
| A | (5) Comparison | 4/1 | 2.96 | 3.42 | 3.46 | 3.46 |
| B | Coupler(a) Comparison | 8/1 | 1.88 | 2.49 | 2.81 | 2.91 |
| C | Coupler(b) | 4/1 | 2.79 | 3.33 | 3.40 | 3.38 |

These results show that the coupler which is used in the method of the present invention can provide higher sensitivity, gradation and maximum color density in comparison with Coupler (b) used in the comparison sample in which the active methylene group is unsubstituted, even when the silver halide/coupler ratio decreases to about ½, and that the coupler according to the present invention can provide a sufficient color density using a short developing time period and thus the total processing time can be shortened. As is evident from these results the coupler of the present invention has a greater coupling reactivity than a coupler having an unsubstituted active methylene group. Also, comparing Sample A in which Coupler (5) of the present invention was used with Sample C containing Coupler (b) which has a releasable group similar to that of Coupler (5), it can be seen that the coupler of the present invention provides a low fog density in spite of its high coupling reactivity.

EXAMPLE 2

Samples A, B and C prepared as described in Example 1 were subjected to sensitometric stepwise exposure and processed in the following manner.

| Processing Step | Temperature (° C) | Time (min) |
| --- | --- | --- |
| 1. Color Development | 30 | 5 |
| 2. Stopping | 30 | 2 |
| 3. Wash | 30 | 2 |
| 4. Blixing | 30 | 6 |
| 5. Wash | 30 | 5 |

The compositions of the processing solutions used were as follows:

| Color Developer Solution B | |
| --- | --- |
| Benzyl Alcohol | 12.0 ml |
| Diethylene Glycol | 3.5 ml |
| Sodium Hexametaphosphate | 2.0 g |
| Sodium Sulfite (anhydrous) | 2.0 g |
| Sodium Carbonate (monohydrate) | 27.5 g |
| Hydroxylamine Sulfate | 2.0 g |
| 4-Amino-3-N-ethyl-N-(β-methanesulfonamido-ethyl)anilino Sesquisulfate (monohydrate) | 4.0 g |

-continued

| | |
|---|---|
| Potassium Bromide | 1.0 g |
| Water to make | 1,000 ml |
| Stopping Solution | |
| Sodium Thiosulfate | 10.0 g |
| Ammonium Thiosulfate (70%) | 30.0 ml |
| Sodium Acetate | 5.0 g |
| Acetic Acid | 30.0 ml |
| Potassium Alum | 15.0 g |
| Water to make | 1,000 ml |
| Blixing Solution | |
| Ferric Sulfate | 20.0 g |
| Ethylenediaminetetraacetic Acid Disodium Salt (dihydrate) | 36.0 g |
| Sodium Carbonate (monohydrate) | 17.0 g |
| Sodium Sulfite | 5.0 g |
| Ammonium Thiosulfate (70%) | 100.0 ml |
| Boric Acid | 5.0 g |
| Water to make | 1,000 ml |

After the processing, the optical density of these samples to blue light were measured. Then these samples were immersed in a 1.5% aqueous potassium ferricyanide solution for 2 minutes, washed with water for 10 minutes and dried. The optical densities of the samples to blue light were again measured. The results obtained are shown in Table 3.

TABLE 3

| | | Treatment with 1.5% Aqueous Potassium Ferricyanide Solution | | | | | |
|---|---|---|---|---|---|---|---|
| | | Before | | | After | | |
| Sample | Coupler | Fog | Gamma | Maximum Density | Fog | Gamma | Max. Density |
| A | (5) | 0.18 | 2.74 | 3.37 | 0.18 | 2.75 | 3.37 |
| B | (a) | 0.10 | 1.48 | 2.16 | 0.11 | 1.85 | 2.64 |
| C | (b) | 0.20 | 2.68 | 3.32 | 0.20 | 2.70 | 3.33 |

Next, the maximum transmission densities to near infrared light of Samples A, B and C obtained upon processing for different periods of blixing time were measured using a filter having an absorption maximum at 750 nm and the results shown in Table 4 were obtained.

TABLE 4

| Sample | Coupler | Coating Amount of Silver (g/m$^2$) | Blixing Time (min) | | |
|---|---|---|---|---|---|
| | | | 2 | 4 | 6 |
| A | (5) | 87.0 × 10$^{-2}$ | 0.10 | 0.04 | 0.03 |
| B | (a) | 187.0 × 10$^{-2}$ | 0.37 | 0.26 | 0.14 |
| C | (b) | 88.2 × 10$^{-2}$ | 0.15 | 0.06 | 0.04 |

From the results shown in Table 3, it is apparent that in the cases of using a coupler having a substituted active methylene group the formation of dye images is completed after the color development and blixing steps. On the contrary, in the case of using Coupler (a) in which the active methylene group is unsubstituted, the formation of the dye image is finished to an extent of about 80% after these steps and the remainder of the reaction products are present in a colorless form. To convert completely the colorless reaction products to dyes, an after treatment with a strong oxidizing agent is required. Therefore, the use of the coupler of the present invention results in a marked shortening of the color processing time.

Also, from the results shown in Table 4, it is clear that in using coupler in the present invention the developed silver formed during color development can be removed easily and rapidly using a blixing solution containing both a weak oxidizing agent and a silver complex forming agent and that improved color reproduction and transparency of the color images can be obtained

EXAMPLE 3

A uniform solution prepared by heating on a steam bath a mixture of 61.5 g the above-described Coupler (20), α-pivaloyl-α-[5-(4-carboxyphenoxy)-1-methyl-3-hydantoinyl]-2-chloro-5-[γ-(2,4-di-tert-amylphenoxy)butyramido]acetanilide, 60 ml of di-n-butyl-phthalate, 120 ml of ethyl acetate and 3.0 g of sodium dinonylnaphthalene sulfonate was added to 600 ml of an aqueous solution containing 60 g of gelatin and the mixture was stirred and then agitated vigorously in a high speed agitator for 30 minutes. The couplers were finely dispersed together with the solvents.

All of the coupler dispersion was added to 1 kg of a photographic emulsion containing 75 g of gelatin and 56.7 g of silver iodobromide (iodide content: 3.0 mol %), and then 45 ml of a 3% acetone solution of triethylene phosphoramide, as a hardener, was added. After adjusting the pH to 6.0, the mixture was coated on a cellulose triacetate film support in a dry thickness of 6.0 microns to prepare a photographic light-sensitive material. This material was designated Sample D.

Also, a photographic light-sensitive material was prepared by carrying out the same procedures as described for Sample D except that the amount of di-n-butyl phthalate was varied to 12 ml. This material was designated Sample E.

For comparison, a photographic light-sensitive material was prepared by carrying out the same procedures as described for Sample D except that 55.0 g of Coupler (c), α-pivaloyl-α-(1-benzyl-3-hydantoinyl)-2-chloro-5-[γ-(2,4-di-tert-amylphenoxy)-butyramido]acetanilide, which is a coupler of the type described in Japanese Patent Application OPI No. 29,432/1973 was used in place of Coupler (20), and the amount of the di-n-butyl phthalate was changed to 55 ml. This material was designated Sample F.

Furthermore, Sample G was prepared by carrying out the same procedures as described for Sample F except that the amount of the di-n-butyl phthalate was changed to 11 ml.

Samples D, E, F and G were subjected to a stepwise exposure and processed using the same process as described in Example 1 except that color development was carried out at 24° C for 12 minutes using Color Developer Solution B described in Example 2.

After processing, the transmission optical density to blue light of these samples was measured to provide the results shown in Table 5.

TABLE 5

| Sample | Coupler | Di-n-butyl Phthalate/ Coupler Ratio (g/ml) | Fog | Sensi-* tivity | Gamma | Maximum Density |
|---|---|---|---|---|---|---|
| D | (20) | 1.0 | 0.14 | 100 | 2.23 | 2.48 |
| E | (20) | 0.2 | 0.12 | 99 | 2.15 | 2.42 |
| F | (c) | 1.0 | 0.15 | 99 | 2.19 | 2.44 |
| G | (c) | 0.2 | 0.12 | 97 | 1.77 | 2.05 |

*Relative value of exposure amount required to produce a density of fog + 0.10

These samples were stored under the conditions of 60° C and 75% RH for two weeks, and the transmission optical density to blue light was measured to provide the results shown in Table 6.

TABLE 6

| Sample | Di-n-butyl Phthalate/ Coupler Ratio (g/ml) | Rate of Remaining Color Image* (%) | | |
|---|---|---|---|---|
| | | Do=0.5 | 1.0 | 2.0 |
| D | 1.0 | 98 | 98 | 99 |
| E | 0.2 | 99 | 100 | 100 |
| F | 1.0 | 96 | 97 | 98 |
| G | 0.2 | 97 | 98 | 98 |

*(Optical density after storage under conditions of high temperature and high humidity/Optical density (do) of fresh sample) × 100

From these results shown in the above tables, it is evident that the coupler used in the present invention is superior in the photographic properties of the color image formed upon color development and in the stability of the yellow color image, particularly the durability under conditions of high temperature and high humidity. Further the coupler can be dispersed in a stable and fine state even when the amount of the high boiling organic solvent used is decreased and the photographic properties and the stability of the color image are not adversely affected by the amount of the high boiling organic solvent. The lower dependence on the amount of high boiling organic solvent is quite advantageous in using the coupler in a photographic light-sensitive material since the amount of the organic solvent incorporated into an emulsion layer can be decreased and thus the physical properties of the emulsion layer are improved, for example, an improvement in the abrasion resistance of the layer, a decrease in exuding of the organic solvent from the layer, and the like. Furthermore, the sharpness of color images is improved due to the decrease in the thickness of the layer.

EXAMPLE 4

Samples D, E, F and G prepared as described in Example 3 were subjected to a stepwise exposure and processed in the same manner as described in Example 1 except that the color development step was carried out at 24° C for 12 minutes using each of the color developer solutions which were prepared by modifying Color Developer Solution B described in Example 2 as set forth below.

Color Developer Solution I:
A 1N sodium hydroxide solution or 1N sulfuric acid solution was added to the Color Developer Solution B described in Example 2 to adjust the solution to a pH of 10.1.

Color Developer Solution II:
The amount of benzyl alcohol in Color Developer Solution B described in Example 2 was changed to 2.0 ml per liter of the color developer solution and the pH was adjusted to 10.1.

Color Developer Solution III:
Dilute sulfuric acid was added to the Color Developer Solution B described in Example 2 to adjust the solution to a pH of 9.8

After processing, the transmission optical density to blue light of Samples D, E, F and G was measured and the photographic properties shown in Table 7 were obtained.

TABLE 7

| Color Developer Solution | Sample | Coupler | Fog | Sensi-* tivity | Gamma | Maximum Density |
|---|---|---|---|---|---|---|
| I | D | (20) | 0.14 | 100 | 2.23 | 2.48 |
| I | E | (20) | 0.12 | 99 | 2.15 | 2.42 |
| I | F | (c) | 0.15 | 99 | 2.19 | 2.44 |
| I | G | (c) | 0.12 | 97 | 1.77 | 2.05 |
| II | D | (20) | 0.13 | 100 | 2.18 | 2.45 |
| II | E | (20) | 0.11 | 98 | 2.07 | 2.37 |
| II | F | (c) | 0.14 | 97 | 2.04 | 2.40 |
| II | G | (c) | 0.10 | 95 | 1.51 | 1.86 |
| III | D | (20) | 0.13 | 99 | 2.16 | 2.43 |
| III | E | (20) | 0.11 | 98 | 2.02 | 2.33 |
| III | F | (c) | 0.13 | 96 | 1.90 | 2.34 |
| III | G | (c) | 0.09 | 94 | 1.42 | 1.75 |

*Relative value of exposure amount required to produce a density of fog + 0.10, when the value obtained from Sample D processed with Color Developer Solution I was assumed to be 100.

From the results shown in Table 7, it is clear that the coupler of the present invention is less dependent on the pH and the amount of benzyl alcohol in the color developer solution used. Thus color photographic materials which are stable and not affected by variations in the pH of the color developer solution can be provided. Also, since the amount of benzyl alcohol in color developer solutions can be decreased it is expected that the biological oxygen demand (BOD) decreases in water and environmental pollution is prevented.

EXAMPLE 5

A solution prepared by heating at 40° C a mixture of 32.0 g of the above-described Coupler (2), α-pivaloyl-α-(1-benzyl-5-methoxy-3-hydantoinyl)-2chloro-5-[γ-(2,4-di-tert-amylphenoxy)butyramido]acetanilide, 24 ml of di-n-butylphthalate and 60 ml ethyl acetate was added to 300 ml of an aqueous solution containing 1.5 g of sodium p-dodecylbenzene sulfonate and 30 g of gelatin. The mixture was stirred and then passed twice through a milk-homogenizer. The couplers were finely dispersed together with the solvents.

All of the coupler dispersion was mixed with 500 g of a photographic emulsion containing 28.2 g of silver iodobromide (iodide content: 2 mol %) and 40 g of gelatin, and then 20 ml of a 3.5% aqueous solution of 2-hydroxy-4,6-dichloro-s-triazine sodium salt, as a hardener, was added. After adjusting the pH to 6.5, the mixture was coated in a dry thickness of 3.5 microns on a photographic paper laminated with polyethylene on both surfaces.

On this layer a gelatin solution was coated in a dry thickness of 1.0 micron as a second layer. A green-sensitive silver halide emulsion layer containing a magenta color forming coupler (d), 1-(2,6-dichloro-4-methoxyphenyl)-3-{3-[α-(2,4-di-tert-amylphenoxy)-butyramido]benzamido}- 5-pyrazolone, was then coated in a dry thickness of 3.5 microns as a third layer. A gelatin solution containing 2-(2'-benzotriazolyl)-4,6-dibutyl-phenol as an ultraviolet absorbing agent was coated in a dry thickness of 2.5 microns as a fourth layer. A red-sensitive silver halide emulsion layer containing a cyan color forming coupler (e), 1-hydroxy-4-chloro-N-dodecyloxypropyl-2-naphthamide, was coated in a dry thickness of 4.0 microns as a fifth layer. Further, a gelatin solution was coated in a dry thickness of 0.5 micron as an uppermost layer, thereby preparing a color printing paper.

The color printing paper was image-exposed through a color negative as an original and processed in the following manner.

| Processing Step | Temperature (° C) | Time (minutes) |
|---|---|---|
| Color Development | 30 | 6 |
| Stopping | 30 | 2 |
| Wash | 30 | 2 |
| Blixing | 30 | 2 |
| Wash | 30 | 2 |
| Stabilizing | 30 | 2 |

The processing solutions employed had the following compositions, respectively.

| Color Developer Solution | |
|---|---|
| Benzyl Alcohol | 12.0 ml |
| Diethylene Glycol | 3.5 ml |
| Sodium Hydroxide | 2 g |
| Sodium Sulfite | 2 g |
| Potassium Bromide | 0.4 g |
| Sodium Chloride | 1 g |
| Boric Acid | 4 g |
| Hydroxylamine Sulfate | 2 g |
| Ethylenediaminetetraacetic Acid Disodium Salt (dihydrate) | 2 g |
| 4-Amino-3-methyl-N-ethyl-N-($\beta$-methanesulfonamidoethyl)aniline Sesquisulfate (monohydrate) | 5 g |
| Water to make | 1,000 ml |
| Stopping Solution | |
| Sodium Thiosulfate | 10 g |
| Ammonium Thiosulfate (70%) | 30 ml |
| Sodium Acetate | 5 g |
| Acetate Acid | 30 ml |
| Potassium Alum | 15 g |
| Water to make | 1,000 ml |
| Blixing Solution | |
| Ferric Sulfate | 20 g |
| Ethylenediaminetetraacetic Acid Disodium Salt (dihydrate) | 36 g |
| Sodium Carbonate (monohydrate) | 17 g |
| Sodium Sulfite | 5 g |
| Ammonium Thiosulfate (70%) | 100 ml |
| Boric Acid | 5 g |
| pH adjusted to 6.8 | |
| Water to make | 1,000 ml |

The color print thus-obtained had a clear color due to the good silver removal property and exhibited excellent color reproducibility. The yellow dye image had an absorption maximum at 445 nm.

The color print was directly exposed to sun light for 14 days, and the density decreases for the yellow dye image were 0.06 in the area of an initial reflection density of 1.0. Also, the color print was stored under high temperature and high humidity conditions of 60° C, 75% RH for 14 days, and substantially no density decrease was observed.

EXAMPLE 6

A solution prepared by heating at 40° C a mixture of 40.0 g of the above-described Coupler (7), $\alpha$-(2-methylbenzoyl)-$\alpha$-(1-benzyl-5-methoxy-3-hydantoinyl)-2-chloro-5-dodecyloxy-carbonylacetanilide, 40 ml of tris(2-ethylhexyl)phosphate, 2.0 g of 2,5-dioctyl-hydroquinone and 80 ml of ethyl acetate was added to 400 ml of an aqueous solution containing 4.0 g of sodium p-dodecylbenzene sulfonate and 40 g of gelatin. The mixture was stirred and then passed twice through a milk-homogenizer to prepare a coupler dispersion.

All of the coupler dispersion was mixed with 1 kg of a photographic reversal emulsion containing 52.3 g of silver iodobromide (iodide content: 5.0 mol %) and 75 g of gelatin, and then 12 ml of a 4% aqueous solution containing 2-hydroxy-4,6-dichloro-s-triazine sodium salt, as a hardener, was added. After adjusting the pH to 6.0, the mixture was coated on a polyethylene terephthalate film in a dry thickness of 5.0 microns to prepare a photographic light-sensitive material. The coating amount of silver in the photographic material was $80.4 \times 10^{-2}$ g/m$^2$.

The photographic light-sensitive material was subjected to a stepwise exposure and processed in the following manner.

| | Processing Step | Temperature (° C) | Time (sec) |
|---|---|---|---|
| 1. | First Development | 40 | 5 |
| 2. | Color Development | 40 | 15 |
| 3. | Stopping | 40 | 10 |
| 4. | Bleach-Stabilizing | 40 | 90 |

The compositions of the processing solutions employed were as follows

| First Developer Solution | |
|---|---|
| 4-(N-Methylamino)phenol Sulfate | 5.0 g |
| Hydroquinone | 15.0 g |
| Sodium Sulfite | 80.0 g |
| Sodium Carbonate (monohydrate) | 41.0 g |
| Potassium Bromide | 4.0 g |
| Sodium Hydroxide | 1.0 g |
| Sodium Thiocyanate | 1.5 g |
| Water to make | 1,000 ml |
| Color Developer Solution | |
| Sodium Sulfite | 5.0 g |
| 4-Amino-3-methyl-N-ethyl-N-($\beta$-hydroxyethyl)-aniline Sulfate | 10.0 g |
| Trisodium Phosphate (dodecahydrate) | 100.0 g |
| Tri(hydroxymethyl)nitromethane | 3.0 g |
| Ethylenediamine (70% aqueous solution) | 11.0 ml |
| Sodium Hydroxide | 0.1 g |
| Water to make | 1,000 ml |
| Stopping Solution | |
| Sodium Sulfite | 40.0 g |
| Disodium Phosphate (dihydrate) | 15.0 g |
| Sodium Sulfate | 120.0 g |
| Water to make | 1,000 ml |
| Bleach-Stabilizing Solution | |
| Iron (III)-Ethylenediaminetetraacetic Acid Disodium Salt (monohydrate) | 36.0 g |
| Ammonium Thiosulfate | 100.0 g |
| Sodium Sulfite | 7.0 g |
| Potassium Metabisulfite | 15.0 g |
| Sodium Phosphate | 20.0 g |
| Sodium Carbonate (monohydrate) | 6.0 g |
| Water to make | 1,000 ml |

In order to evaluate the silver removal property, the transmission density of the reversal color photographic image thus-obtained at the maximum density area of the yellow color image was measured using a filter having an absorption maximum at 750 nm and a value of 0.04 was obtained. Also, the yellow reversal image had an absorption maximum at 452 nm.

From the result, it is evident that the coupler of the present invention has a good applicability to a super rapid processing method and silver removal is completed in a shortened period of bleaching time. Thus the reversal color image obtained has a clear color and a superior color reproducibility.

EXAMPLE 7

To a silver iodobromide emulsion (iodide content: 2.5 mol %), a 4% aqueoues solution of 2-hydroxy-4,6-dichloro-s-triazine sodium salt was added in the amount of 1.0 % based on the gelatin in the emulsion, and the emulsion was coated in a dry thickness of 4.0 microns and a silver coating amount of $125 \times 10^{-2}$ g/m$^2$ to prepare a film. The film was subjected to exposure using a wedge for sensitometry and developed at 27° C for 4 minutes using the color developer solution set forth below, and then fixed, washed, bleached, washed, fixed and washed in the same manner as described in Example 1 to provide a yellow dye image.

| Color Developer Solution | |
|---|---|
| Sodium Sulfite | 1.0 g |
| 4-Amino-3-methyl-N,N-diethylaniline Hydrochloride | 2.0 g |
| Sodium Carbonate (monohydrate) | 22.5 g |
| Potassium Bromide | 1.0 g |
| Coupler (8), α-Pivaloyl-α-(1-methyl-5-methoxy-3-hydantoinyl)-2-chloroacetanilide | 2.0 g |
| Acetone | 20.0 ml |
| Sodium Hydroxide (2N aqueous solution) | 25.0 ml |
| Water to make | 1,000 ml |

The yellow dye image had an absorption maximum at 448 nm.

EXAMPLE 8

A solution prepared by heating at 70° C a mixture of 52.5 g of the above-described Coupler (26), α-(4-methoxybenzoyl)-α-(5-dodecyloxy-1-methyl-3-hydantoinyl)-3,5-dicarboxyacetanilide, 80 ml of N,N-diethyldodecylamide and 100 ml of cyclohexanone was added to 500 ml of an aqueous solution containing 4.0 g of sodium p-dodecylbenzene sulfonate and 50 g of gelatin. The mixture was stirred and then passed five times through a pre-heated colloid mill. The couplers were finely dispersed together with the solvents.

All of the coupler dispersion was mixed with 1 kg of a photographic emulsion containing 76.0 g of silver iodobromide (iodide content: 5.0 mol %) and 65 g of gelatin, and then 25 ml of a 4% aqueous solution of 2-hydroxy-4,6-dichloro-s-triazine sodium salt, as a hardener, was added. The mixture was coated on a cellulose triacetate film support in a dry thickness of 5.0 microns. On the coating a gelatin solution was coated in a dry thickness of 1.0 micron, as a protective layer, thus preparing a light-sensitive material.

On a cellulose triacetate film support the following layers were coated, in order, to prepare an image receiving material.

1. Neutralizing layer containing 300 mg/100 cm² of the butyl half ester of a (1:1 molar ratio) copolymer of vinyl methyl ether and maleic anhydride, 60 mg/100 cm² of 1,4-bis(2',3'-epoxypropoxy)butane and 21 mg/100 cm² of hexahydro-1,3,5-triacryloyl-s-triazine.

2. Neutralizing rate control layer containing 45 mg/100 cm² of a copolymer of n-butylacrylate and β-hydroxyethylmethacrylate (molar ratio: about 1:1).

3. Image receiving layer containing 18 mg/100 cm² of cetyl-tri-n-butylammonium chloride, 40 mg/100 cm² of gelatin and 2 mg/100 cm² of tetramethylol urea.

4. Covering layer having a thickness of about 0.5 micron prepared by coating a 1% acetone solution of polyethyleneglycol monocetyl ether.

A processing solution having the composition set forth below was prepared and incorporated into a rupturable container. The container was prepared by folding a film laminated polyethylene, aluminum, cellophane and polyethylene and heat-sealing so as to form a container for the processing solution. The preparation and the incorporation of the processing solution into the container was carried out under Freon gas.

| | |
|---|---|
| Water | 100 ml |
| Ascorbic Acid | 20 mg |
| 4-Amino-3-methyl-N-ethyl-N-(β-hydroxyethyl)-aniline Sulfate (monohydrate) | 2.8 g |
| 6-Nitrobenzimidazole Nitrate | 15 mg |
| Sodium Hydroxide | 4 g |

-continued

| | |
|---|---|
| Sodium Carboxymethyl Cellulose | 3.5 g |
| Titanium Dioxide | 45 g |

The light-sensitive material and the image receiving material described above were cut into an appropriate size for testing, the coated surfaces of each material were faced toward each other, and between these materials, at one of the edges, the container retaining the processing solution was tightly positioned.

The film unit thus-prepared was exposed and passed through a pair of pressure rollers to rupture the container and spread uniformly the processing solution.

After three minutes, a clear yellow dye image formed on the image receiving layer was observed.

EXAMPLE 9

A uniform solution prepared by heating at 60° C a mixture of 10 g of the above-described Coupler (1), α-pivaloyl-α-(5-methoxy-1-phenyl-3-hydantoinyl)-2-methoxy-5-[N-γ-(2,4-di-tert-amylphenoxy)propylsulfamoyl]acetanilide, 10 ml of di-n-butyl phthalate and 20 ml of butyl acetate was added to 100 ml of an aqueous solution containing 0.5 g of sodium dodecylbenzene sulfonate and 10 g of gelatin. The mixture was stirred and then agitated vigorously in a high speed agitator for 20 minutes. The couplers were finely dispersed together with the solvents.

92 g of the coupler dispersion was added to 100 g of a photographic emulsion containing $3.0 \times 10^{-2}$ mole of silver iodobromide (iodide content: 2 mol %) and 6.5 g of gelatin, and then 7 ml of a 2% aqueous solution of 2-hydroxy-4,6-dichloro-s-triazine sodium salt, as a hardener, was added. After adjusting the pH to 6.0, the mixture was coated on a cellulose triacetate film support in a dry thickness of 6.0 microns to prepare a photographic light-sensitive material.

Coupler dispersions were prepared in the same manner as described above using each of the above-described Couplers (4), (10), (12) and (15), and 110 g, 107 g, 103 g and 80 g of the coupler dispersions, respectively, were added to the same photographic emulsion as described above to prepare photographic light-sensitive materials.

These films were subjected to a stepwise exposure for sensitometry and processed in the same manner as described in Example 1 to provide yellow color images. The spectral absorption properties of these yellow color images were measured using a spectrophotometer and the absorption maxima as shown in Table 8 were obtained.

TABLE 8

| Coupler | Absorption Maximum |
|---|---|
| | (nm) |
| (1) | 447 |
| (4) | 448 |
| (10) | 453 |
| (12) | 457 |
| (15) | 455 |

While the invention has been described in detail and with reference to specific embodiments thereof, it will be apparent to one skilled in the art that various changes and modifications can be made therein without departing from the spirit and scope thereof.

What is claimed is:

1. A method of forming color photographic images which comprises developing an imagewise exposed photographic silver halide emulsion layer with a primary aromatic amino color developing agent in the presence of a yellow color forming coupler represented by the following general formula (I):

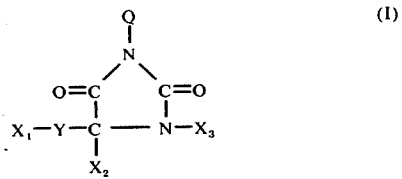

wherein $X_1$ represents a hydrogen atom, an alkyl group, an aryl group, a 2-tetrahydropyranyl group, a 2-pyridyl group, a 4-pyridyl group or an acyl group having up to about 35 carbon atoms; $X_2$ represents a hydrogen atom, an alkyl group or an aryl group; $X_3$ represents a hydrogen atom, an alkyl group, an aryl group or an acyl group having up to about 35 carbon atoms; Y represents an oxygen atom or a sulfur atom; $X_2$ and $X_3$ can combine to form a pyrrolidine ring or a piperidine ring; and Q represents a residue of an α-acylacetamide yellow color forming coupler in which one hydrogen atom attached to the active methylene group of the coupler is eliminated.

2. The method of forming color photographic images as claimed in claim 1, wherein said alkyl group represented by $X_1$ is a straight-chain, a branched-chain or cyclohexyl and contains up to 35 carbon atoms.

3. The method of forming color photographic images as claimed in claim 1, wherein said aryl group represented by $X_1$ is a phenyl group or a naphthyl group.

4. The method of forming color photographic images as claimed in claim 1, wherein said alkyl group represented by $X_2$ is a straight-chain, a branched-chain or cyclohexyl and contains up to 35 carbon atoms.

5. The method of forming color photographic images as claimed in claim 1, wherein said aryl group represented by $X_2$ is a phenyl group or a naphthyl group.

6. The method of forming color photographic images as claimed in claim 1, wherein said alkyl group represented by $X_3$ is a straight-chain, a branched-chain or cyclohexyl and contains up to 35 carbon atoms.

7. The method of forming color photographic images as claimed in claim 1, wherein said aryl group represented by $X_3$ is a phenyl group or a naphthyl group.

8. The method of forming color photographic images as claimed in claim 1, wherein said yellow color forming coupler has the general formula (II):

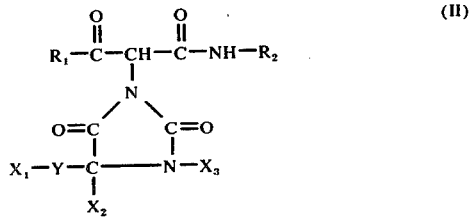

wherein $R_1$ represents an aliphatic group, an aromatic group or a heterocyclic group; $R_2$ represents an aromatic group or a heterocyclic group; and $X_1$, $X_2$, $X_3$ and Y each has the same meaning as defined in claim 1.

9. The method of forming color photographic images as claimed in claim 8, wherein said aliphatic group represented by $R_1$ is a tert-butyl group.

10. The method of forming color photographic images as claimed in claim 8, wherein said aromatic group represented by $R_1$ is a phenyl group or a phenyl group substituted with an electron-donating group.

11. The method of forming color photographic images as claimed in claim 8, wherein said aromatic group represented by $R_2$ is a phenyl group in which one of the ortho positions is substituted with a halogen atom, an alkyl group, an alkoxy group, an aryloxy group or an N-substituted amino group.

12. The method of forming color photographic images as claimed in claim 1, wherein said yellow color forming coupler has the general formula (III):

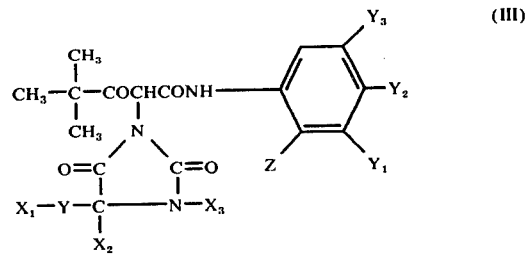

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; and $X_1$, $X_2$, $X_3$ and Y each has the same meaning as defined in claim 1.

13. The method of forming color photographic images as claimed in claim 1, wherein said yellow color forming coupler has the general formula (IV):

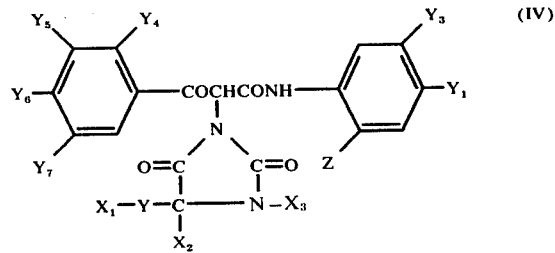

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; $Y_4$, $Y_5$, $Y_6$, and $Y_7$ each represents a hydrogen atom, an alkyl group, an alkoxy group, an aryloxy group, an amino group or an acylamino group; and $X_1$, $X_2$, $X_3$ and Y each has the same meaning as defined in claim 1.

14. The method of forming color photographic images as claimed in claim 1, wherein said yellow color forming coupler is present in said exposed photographic silver halide emulsion layer.

15. The method of claim 1, wherein said acyl group represented by $X_1$ is acetyl, propionyl, octanoyl, tetradecanoyl, stearoyl, benzoyl or α-(2,4-di-tert-amylphenoxy)butyryl.

16. The method of claim 1, wherein said acyl group represented by $X_3$ is acetyl, propionyl, octanoyl, tetradecanoyl, stearoyl, benzoyl or α-(2,4-di-tert-amylphenoxy)butyryl.

17. The method of forming color photographic image as claimed in claim 15, wherein the alkyl groups for $X_1$, $X_2$ and $X_3$ are methyl, ethyl, propyl, isopropyl, amyl, isoamyl, hexyl, 1-methylpentyl, 2-methylpentyl, heptyl, 1-methylhexyl, 2-methylhexyl, 3-methylhexyl, 5-methylhexyl, octyl, 2-ethylhexyl, nonyl, isononyl, decyl, undecyl, dodecyl, tetradecyl, hexadecyl, octadecyl, cyclohexyl, benzyl, phenethyl, allyl, oleyl, 2-methoxyethyl, 2-hydroxyethyl, carboxymethyl, 2-carboxyethyl, 3-phenoxypropyl, 2-(4-tert-butylphenoxy)isopropyl, and cinnamyl.

18. The method of claim 1, wherein said aryl groups are phenyl or naphthyl.

19. The method of claim 1, wherein said alkyl groups are straight chain alkyl groups having up to about 35 carbon atoms.

20. The method of claim 1, wherein said alkyl groups are branched chain alkyl groups having up to about 35 carbon atoms.

21. The method of claim 1, wherein Y represents an oxygen atom.

22. The method of claim 1, wherein Y represents a sulfur atom.

23. A color photographic light-sensitive material which comprises a silver halide emulsion containing a yellor color forming coupler represented by the following general formula (I):

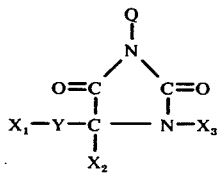

wherein $X_1$ represents a hydrogen atom, an alkyl group, an aryl group, a 2-tetrahydropyranyl group, a 2-pyridyl group, a 4-pyridyl group or an acyl group having up to about 35 carbon atoms; $X_2$ represents a hydrogen atom an alkyl group or an aryl group; $X_3$ represents a hydrogen atom, an alkyl group, an aryl group or an acyl group having up to about 35 carbon atoms; Y represents an oxygen atom or a sulfur atom; $X_2$ and $X_3$ can combine to form a pyrrolidine ring or a piperidine ring; and Q represents a residue of an α-acylacetamide yellow color forming coupler in which one hydrogen atom attached to the active methylene group of the coupler is eliminated.

24. The color photographic light-sensitive material of claim 23, wherein said alkyl group represented by $X_1$ is a straight-chain, a branched-chain or cyclohexyl and contains up to 35 carbon atoms.

25. The color photographic light-sensitive material of claim 23, wherein said aryl group represented by $X_1$ is a phenyl group or a naphthyl group.

26. The color photographic light-sensitive material of claim 23, wherein said alkyl group represented by $X_2$ is a straight-chain, a branched-chain or cyclohexyl and contains up to 35 carbon atoms.

27. The color photographic light-sensitive material of claim 23, wherein said aryl group represented by $X_2$ is a phenyl group or a naphthyl group.

28. The color photographic light-sensitive material of claim 23, wherein said alkyl group represented by $X_3$ is a straight-chain, a branched-chain or cyclohexyl and contains up to 35 carbon atoms.

29. The color photographic light-sensitive material of claim 23, wherein said aryl group represented by $X_3$ is a phenyl group or a naphthyl group.

30. The color photographic light-sensitive material of claim 23, wherein said yellow color forming coupler has the general formula (II):

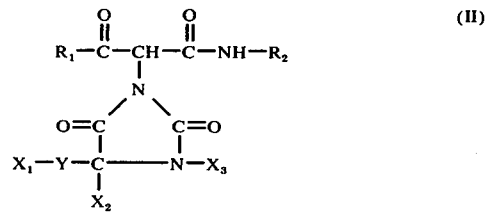

wherein $R_1$ represents an aliphatic group, an aromatic group or a heterocyclic group; $R_2$ represents an aromatic group or a heterocyclic group; and and $X_1$, $X_2$, $X_3$ and Y each has the same meaning as defined in claim 23.

31. The color photographic light-sensitive material of claim 30, wherein said aliphatic group represented by $R_1$ is a tert-butyl group.

32. The color photographic light-sensitive material of claim 30, wherein said aromatic group represented by $R_1$ is a phenyl group or a phenyl group substituted with an electron-donating group.

33. The color photographic light-sensitive material of claim 30, wherein said aromatic group represented by $R_2$ is a phenyl group in which one of the ortho positions is substituted with a halogen atom, an alkyl group, an alkoxy group, an aryloxy group or an N-substituted amino group.

34. The color photographic light-sensitive material of claim 23, wherein said yellow color forming coupler has the general formula (III):

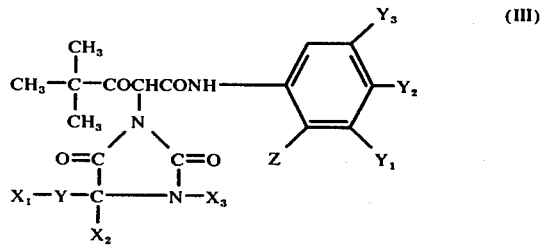

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; and $X_1$, $X_2$, $X_3$ and Y each has the same meaning as defined in claim 19.

35. The color photographic light-sensitive material of claim 23, wherein said yellow color forming coupler has the general formula (VI):

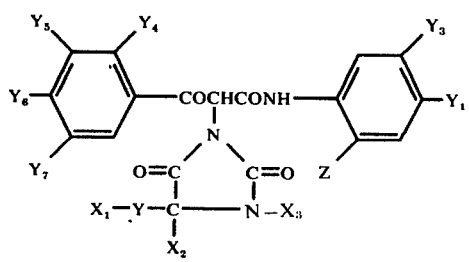
(IV)

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; $Y_4$, $Y_5$, $Y_6$, and $Y_7$ each represents a hydrogen atom, an alkyl group, an alkoxy group, an aryloxy group, an amino group or an acylamino group; and $X_1$, $X_2$, $X_3$ and Y each has the same meaning as defined in claim 23.

* * * * *